United States Patent
Nielsen

(10) Patent No.: US 10,281,392 B2
(45) Date of Patent: May 7, 2019

(54) DETECTION OF INDICATIONS OF PSYCHOACTIVE COMPONENTS IN A LIQUID

(71) Applicant: Drugster ApS, Aarhus C (DK)

(72) Inventor: Ulrik Merrild Nielsen, Brabrand (DK)

(73) Assignee: Drugster ApS, Aarhus (DK)

(*) Notice: Subject to any disclaimer, the term of this patent is extended or adjusted under 35 U.S.C. 154(b) by 0 days.

(21) Appl. No.: 14/899,093

(22) PCT Filed: Jun. 16, 2014

(86) PCT No.: PCT/EP2014/062569
§ 371 (c)(1),
(2) Date: Dec. 16, 2015

(87) PCT Pub. No.: WO2014/202531
PCT Pub. Date: Dec. 24, 2014

(65) Prior Publication Data
US 2016/0131577 A1    May 12, 2016

(30) Foreign Application Priority Data

Jun. 16, 2013   (DK) .................................. 2013 00363

(51) Int. Cl.
*G01N 21/49* (2006.01)
*G01J 3/02* (2006.01)
(Continued)

(52) U.S. Cl.
CPC ............ *G01N 21/49* (2013.01); *G01J 3/0256* (2013.01); *G01J 3/10* (2013.01); *G01J 3/108* (2013.01);
(Continued)

(58) Field of Classification Search
CPC ....................................................... G01N 21/49
See application file for complete search history.

(56) References Cited

U.S. PATENT DOCUMENTS 5,054,487 A    10/1991   Clarke
6,620,626 B1   9/2003    Bodily
(Continued)

FOREIGN PATENT DOCUMENTS

AU    2006200304 A1    9/2006
CN    1918465 A        2/2007
(Continued)

OTHER PUBLICATIONS

International Search Report dated Aug. 29, 2014 in International Application No. PCT/EP2014/062569.
(Continued)

*Primary Examiner* — Michael C Bryant
(74) *Attorney, Agent, or Firm* — Knobbe, Martens, Olson & Bear, LLP

(57) ABSTRACT

A method of contactless detection of indications of psychoactive components in a liquid and an apparatus therefor, by emitting a substantially monochromatic light at least at two different wavelengths and detecting the reflection in a free surface of the liquid by a photo detector, analyzing an output signal from the photo detector to identify output parts caused by light emitted from the first and second emitters, respectively, and determining whether the liquid contains at least one psychoactive component.

22 Claims, 1 Drawing Sheet

(51) Int. Cl.
*G01N 21/3577* (2014.01)
*G01J 3/10* (2006.01)
*G01N 21/51* (2006.01)
*G01N 21/31* (2006.01)

(52) U.S. Cl.
CPC .... *G01N 21/3577* (2013.01); *G01J 2003/104* (2013.01); *G01N 21/51* (2013.01); *G01N 2021/3196* (2013.01); *G01N 2201/0221* (2013.01); *G01N 2201/1293* (2013.01)

(56) References Cited

U.S. PATENT DOCUMENTS

| | | |
|---|---|---|
| 8,106,361 B2 | 1/2012 | Benes |
| 2008/0218733 A1 | 9/2008 | Benes |
| 2013/0329216 A1* | 12/2013 | Patolsky .............. G01N 33/146 356/51 |

FOREIGN PATENT DOCUMENTS

| | | |
|---|---|---|
| CN | 101351688 A | 1/2009 |
| CN | 102834710 A | 12/2012 |
| GB | 2490537 A | 11/2012 |
| JP | 2007-271575 A | 10/2007 |
| WO | WO 2005050149 A2 | 6/2005 |
| WO | WO 2012077110 A2 | 6/2012 |
| WO | WO 2013049085 A1 | 4/2013 |

OTHER PUBLICATIONS

Yang Guoqiang et al., "Study on Discrimination of Brands of Chinese Distilled Spirit Using Near Infrared Transmission, and Reflectance Spectra", World Automation Congress (WAC), 2010, IEEE, Piscataway, NJ, USA, Sep. 19, 2010, pp. 251-256, XP03183364, ISBN: 978-1-4244-9673-0.

Victoria L. Brewster et al., "Identification of the date-rape drug GHB and its precursor GBL by Raman spectroscopy", Drug Testing and Analysis, vol. 1, No. 1, Jan. 1, 2009, pp. 25-31, XP55135381, ISSN: 1942-7603, John Wiley & Sons, Ltd.

James V. Defrancesco et al., "GHB Free Acid: I. Solution Formation Studies and Spectroscopic Characterization by HNMR and FT-IR", Journal of Forensic Sciences, Mar. 1, 2006, pp. 321-329, vol. 51, No. 2, American Academy of Forensic Sciences, Cincinnati, Ohio, US.

International Preliminary Report on Patentability dated Jul. 23, 2015 in International Application No. PCT/EP2014/062569.

Bevan, C. A High-Throughput Screening Method for the Determination of Aqueous Drug Solubility Using Laser Nephelometry in Microliter Plates, Anal Chem, vol. 72, pp. 1781-1787, (2000).

Office Action dated Jun. 4, 2018 in Japanese Patent Application No. 2016-518528.

* cited by examiner

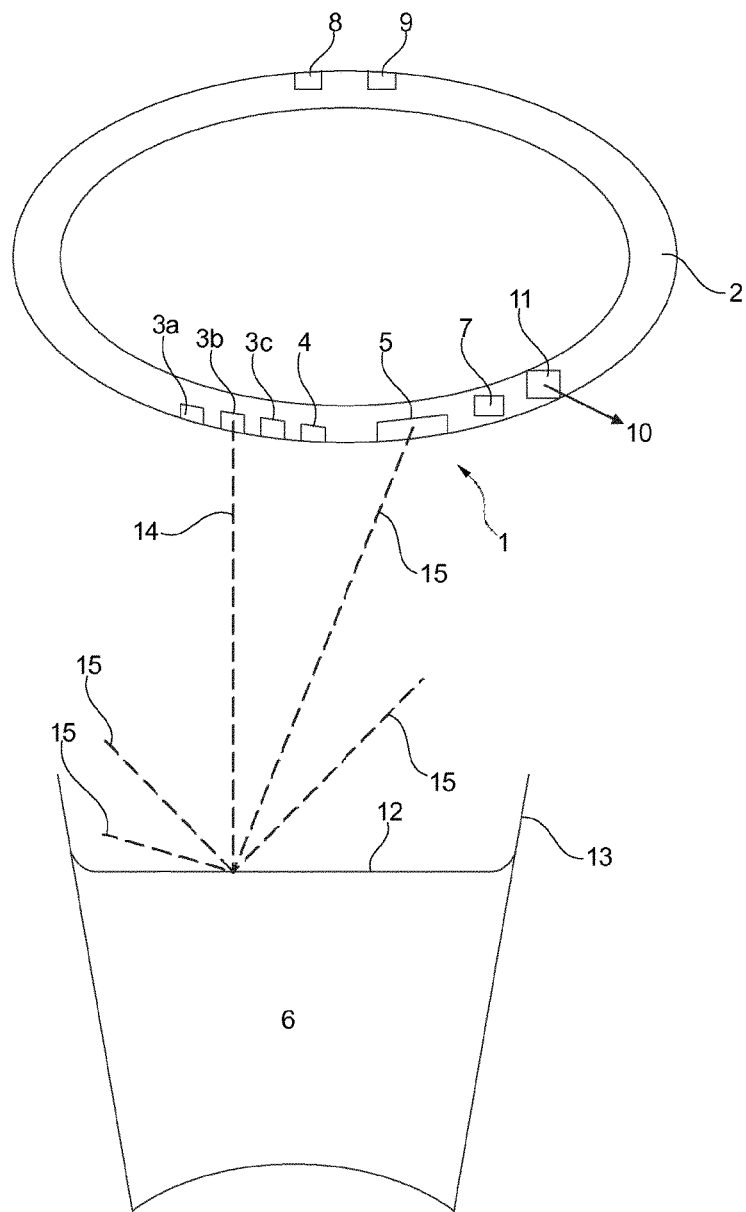

DETECTION OF INDICATIONS OF PSYCHOACTIVE COMPONENTS IN A LIQUID

CROSS REFERENCE TO RELATED APPLICATIONS

This application is the U.S. National Phase Application under 35 U.S.C. § 371 of International Application No. PCT/EP2014/062569, filed Jun. 16, 2014, designating the U.S. and published in English as WO 2014/202531 A1 on Dec. 24, 2014 which claims the benefit of Denmark Patent Application No. PA201300363 DK, filed Jun. 16, 2013. Any and all applications for which a foreign or a domestic priority is claimed is/are identified in the Application Data Sheet filed herewith and is/are hereby incorporated by reference in their entirety under 37 C.F.R. § 1.57.

FIELD

The invention relates to a method for detection of indications of psychoactive components in liquids as well as an apparatus for practicing the method.

BACKGROUND

A number of psychoactive drugs are regularly added to drinks, beverages or other liquids for human consumption in order to place the involuntarily consumer of that psychoactive drug in an incapacitated condition for e.g. theft or sexual assault, popularly known as date drug rape.

Prior art methods of detecting the presence of psychoactive contaminants in a liquid for human consumption includes the an addition of reagents and a following analysis due to a change of features of the reagents, such as increased turbidity or changes on the reagents on a test strip.

It is one object of the present invention to provide a method as well as an apparatus, wherein the possible contents of a psychoactive component in a liquid may be determined without the risk of polluting the liquid with a potentially harmful reagent.

SUMMARY

Disclosed herein is a method of contactless detection of indications of psychoactive components in a liquid, the method comprising the steps of emitting substantially monochromatic light at a first test wavelength by means of a first test light emitter, emitting substantially monochromatic light at a second test wavelength being different from said first wavelength by means of a second test light emitter, detecting reflection of said emitted light in a free surface of said liquid by means of a photo detector, the first and the second light emitters being operated so as to enable a separation of an output signal from the photo detector in an output part caused by light emitted from the first emitter and an output part caused by light emitted from the second emitter, analyzing an output signal from the photo detector to identify a first output part from the photo detector caused by light emitted from the first emitter and a second output part caused by light emitted from the second emitter, and determine from at least said first output part and said second output part indications of whether the liquid contains at least one psychoactive component of a group of psychoactive components.

The light emitters may in a preferred embodiment be Light Emitting Diodes (LED) which emit light in a very narrow band width, which for the present invention is considered to be substantially monochromatic. Alternative light emitters include Laser Diodes.

The indication from the analyses may origin from one of the drugs in the group of psychoactive components or from other drugs than the ones in the group of psychoactive components, e.g. components having a similar chemical structure. However, the presence of psychoactive components in the liquid in an amount sufficient to become psychoactive to a human upon consumption of the liquid will be indicated by the method.

The method may preferably comprising the step of emitting substantially emitting substantially monochromatic light at at least one further wavelength by means of at least one further light emitter, detecting reflection of said emitted light in a free surface of said liquid by means of a photo detector, the light emitters being operated so as to enable a separation of an output signal from the photo detector in output parts caused by light emitted from each of the light emitters, analyzing an output signal from the photo detector to identify further output parts from the photo detector caused by light emitted from said one or more further light emitters, and determine from said output parts indications of whether contains at least one psychoactive component of the group of psychoactive components.

Thus, it is preferred that the method is performed by use of at least a third test light emitter. In a preferred embodiment three or four test light emitters are used, which appear to be sufficient to provide reliable analysis of liquids comprising psychoactive ingredients in an amount that may cause an effect on a human.

The light emitted by one of said further light emitters is preferably selected at a turbidity wavelength in the range of 1400 nm to 1560 nm or 1870 nm to 2050 nm, wherein the output part from the photo detector caused by light emitted from said further light emitter is applied to determine the turbidity of the liquid.

The group of psychoactive components comprises in a preferred embodiment at least zolpidem, ketamine and gamma-hydroxybutyrat, the later also known as GHB or Fantasy. These three components appear to be the most commonly drugs used for the illegal purpose of involuntarily drugging of victims.

A positive finding by means of the method will include a detection of at least these two psychoactive drugs as far as they are present in a concentration sufficient to cause a substantial effect on a human. Zolpidem belongs to the group of non-benzodiazepine Z-drugs together with e.g. zopiclone and zaleplon, and the presence in the liquid of one of these drugs will normally cause the same or at least a similar indication obtained by means of the method.

The group of psychoactive components comprises preferably also gamma-butyrolactone, known as GBL, which is closely related to GHB.

The group of psychoactive components comprises preferably also one or more of flunitrazepam, zopiclone and methylphenidate, known by their trade names of Rohypnol, Imoclone and Ritalin, respectively.

The group of psychoactive components may furthermore comprise one or more of midazolam, temazepam, clonazepam and alprazolam, however, the method does not necessarily provide a distinction between all components or drugs in this group.

The group of psychoactive components comprises preferably also benzodiazepines.

In a preferred embodiment of the present invention, the step of determining from said output parts an indication of whether the liquid contains at least one psychoactive component of a group of psychoactive components is based on a multi variable analysis of test results conducted previously to the present method.

The mutual separation between each of the two, preferably each of the three, test wavelengths is at least 60 nm, preferably at least 90 nm. The method may comprise the use of in particular three and more particular four different test wavelengths with a mutual separation between the wavelengths of at least 60 nm, preferably at least 90 nm, the separation has shown to be advantageous for the output parts pertaining to each of the test light emitters to be sufficiently different to distinguish and identify the presence of psychoactive components in the liquid.

It is preferred that at least the first and the second test wavelength are in the range of 700 to 2500 nm, preferably in the range of 900 and 1800 nm and more preferred in the range of 1000 to 1400 nm, since these are ranges at which the transmittance of the light through water is high.

It is furthermore preferred that a third test wavelength is in the range of 700 to 2500 nm, preferably in the range of 900 and 1800 nm and more preferred in the range of 1000 to 1400 nm.

The method is preferably applied on liquids that contain alcohol, preferably in an amount in the range of 3 to 50 volume percent.

It is advantageous that the present method may be carried out on a liquid, wherein the liquid is suitable for human consumption after detection.

The light emitters and the photo detector are preferably so arranged as to allow diffuse reflection of light from the free liquid surface to reach the photo detector and to avoiding specular reflection from said free liquid surface to reach the photo detector because the specular reflection may disturb the test results. This may be achieved by angling the light emitters and/or the photo detector and/or providing screens around the light emitters and/or the photo detector to avoid specular reflection.

The photo detector may comprise a single or a plurality of photo detecting units.

The present invention furthermore relates to an apparatus for performing the above method.

The apparatus is preferably provided in a handheld unit, such as a bracelet.

The apparatus contains in a preferred embodiment from 2 to 12 test light emitters, preferably from 3 to 8 test light emitters, such as from 3 to 6 test light emitters, since one of the advantages of the present invention is that advanced equipment for detailed spectral analysis of the liquid is made superfluous by the present invention.

At least the first and the second test wavelength of the apparatus are preferably in the range of 700 to 2500 nm, preferably in the range of 900 and 1800 nm and more preferred in the range of 1000 to 1400 nm.

At least a third test wavelength of the apparatus is preferably in the range of 700 to 2500 nm, preferably in the range of 900 and 1800 nm and more preferred in the range of 1000 to 1400 nm.

The present invention also relates to the use of the apparatus for carrying out the method of the invention.

According to a second aspect of the present invention, it relates to a method of detection of indications of psychoactive components in a liquid, the method comprising the steps of emitting substantially monochromatic light at a first test wavelength by means of a first test light emitter, emitting substantially monochromatic light at a second test wavelength being different from said first wavelength by means of a second test light emitter, detecting transmission of said emitted light through said liquid by means of a photo detector, the first and the second light emitters being operated so as to enable a separation of an output signal from the photo detector in an output part caused by light emitted from the first emitter and an output part caused by light emitted from the second emitter, analyzing an output signal from the photo detector to identify a first output part from the photo detector caused by light emitted from the first emitter and a second output part caused by light emitted from the second emitter, and determine from at least said first output part and said second output part indications of whether the liquid contains at least one psychoactive component of a group of psychoactive components.

According to this aspect, the emitted light is transmitted through the liquid, preferably over a distance less than 5 millimeters, such as less than 3 millimeters, e.g. in the range of 0.5 to 2.5 millimeters by means of an apparatus that e.g. is lowered into the container, e.g. a glass, holding the liquid to be tested.

This method may furthermore comprise the step of emitting substantially emitting substantially monochromatic light at at least one further wavelength by means of at least one further light emitter, detecting transmission of said emitted light through said liquid by means of a photo detector, the light emitters being operated so as to enable a separation of an output signal from the photo detector in output parts caused by light emitted from each of the light emitters, analyzing an output signal from the photo detector to identify further output parts from the photo detector caused by light emitted from said one or more further light emitters, and determine from said output parts indications of whether contains at least one psychoactive component of the group of psychoactive components.

The further steps and features described above with respect to the method according to the first aspect and described in claims 3 to 17 may likewise be applied to the method according to the second aspect. The invention also relates to an apparatus for carrying out the method according to the second aspect with the optional features described above with respect to the apparatus for carrying out the method according to the first aspect and described in claims 19 to 22 as well as to the use of such apparatus for carrying out the method according to the second aspect of the present invention.

BRIEF DESCRIPTION OF THE DRAWING

An embodiment of the present invention is depicted in the drawing, of which

FIG. 1 is a sketch of the use of an apparatus according to the present invention.

DETAILED DESCRIPTION

An embodiment of the present invention is shown in FIG. 1, where the detection apparatus 1 is implemented in a bracelet 2 to be worn by the user. In alternative embodiments, the apparatus 1 may be implemented in another movable object, such as the cover of a mobile telephone or a laptop computer, or the apparatus 1 could be arranged stationary at a test location where users may test their drink for the presence of psychoactive drugs. The apparatus 1 comprises three test light sources 3a, 3b, 3c being Light Emitting Diodes (LED) for emitting monochromatic light in the near-infrared range, more particularly with the respective wavelengths of 1300 nm (La), 1460 nm (Lb) and 1550 nm (Lc) for the detection of the presence of a number of psychoactive components, including Gamma-hydroxybutyrate (known as GHB or Fantasy), ketamine and zolpidem. The apparatus furthermore comprises a turbidity light source 4 being a Light Emitting Diode for emitting monochromatic light at a wavelength in the near-infrared range which is most influenced by the presence of suspended particles in the liquid, also known as turbidity, for the example chosen to be 1900 nm where the absorbance by water is high and the reflectivity by the liquid can be expected to increase with the presence of suspended particles in the liquid. The turbidity light source 4 is applied to obtain a measure of the turbidity of the liquid 6 caused by the presence of non-dissolved drug carrier ingredients from tablets containing the psychoactive component or by some psychoactive components that are not dissolved in water or alcohol. The apparatus 1 furthermore comprises a control unit 7 for controlling the operation of the light sources 3a, 3b, 3c, 4 and receiving an output from the photo detector 5, for calculating the possible presence of psychoactive components in the liquid 6 and produce an output accordingly in the form of activating a green light diode 8 or a red light diode 9 and for wirelessly transmitting a set of data 10 to an external receiver by means of a transmitter 11, such as to a mobile telephone (not shown). In an alternative embodiment, the set of data 10 is transmitted to an external receiver which comprises the computer software to determine the possible presence of psychoactive components and provide an output that is transmitted wirelessly to a transceiver 11 of the apparatus 1.

In use of the apparatus 1, the surface 12 of the liquid 6 in the liquid container 13 and the bracelet 2 comprising the apparatus 1 is situated relatively to each other by the user so that the apparatus is able to perform a contactless detection of the contents of the liquid 6. This is done by emitting light 14 from the four light sources 3a, 3b, 3c, 4 and detecting the intensity of the diffusely reflected light 15 from the surface 12 of the liquid 6 by means of the photo detector 5. For the sake of example, only light 14 emitted from one light source 3b of the four light sources 3a, 3b, 3c, 4 and the corresponding diffusely reflected light 15 is shown on the FIGURE.

The control unit 7 operates the four light sources 3a, 3b, 3c, 4 at different switching frequencies so that the output from the photo detector 5 to the control unit 7 is easily separable by means of frequency analysis to output pertaining or being caused by light emitted from each of the four light sources 3a, 3b, 3c, 4 by the control unit 7.

Alternative modes of operating the different lights sources 3a, 3b, 3c, 4 so as to enable separation of the output could be implements based on known techniques.

The analysis of the output from the photo detector 5 pertaining to each of the four light sources 3a, 3b, 3c, 4 is then applied to different parts of analysis:

The part of the output from the photo detector 5 pertaining to the turbidity light source 4 is used in the analysis to indicate the presence of non-dissolved suspended particles in the liquid 6, presumably stemming from only partial dissolution of drug carrier ingredients in tablets containing the psychoactive drug.

Also the turbidity of the liquid may also be assessed from the output parts pertaining from the test light sources. The reflection will increase with the turbidity but may also decrease depending on the spectral features of the possible content of psychoactive components. From an evaluation of the output, the control unit 7 may flash the two coloured diodes 8, 9 for a repetition of the test, possibly with a shorter distance between the apparatus 1 and the free surface 12 of the liquid 6 to be tested to obtain an improved signal to noise ratio, or the control unit 7 may light the red light diode 9 in case the outcome of the evaluation is positive. A positive indication based purely on turbidity may be due to the presence of e.g. fruit juice or milk in the liquid 6, which has natural high contents of suspended particles, or it may be due to only partial dissolution of drug carrier ingredients in tablets containing the psychoactive drug. Thus, an indication of high turbidity may be used to support results signifying the presence of a psychoactive drug in the liquid 6 from the evaluation of the output parts pertaining to the test light sources 3a, 3b, 3c. Alternatively, in case the repeated test has the same outcome, i.e. high turbidity but no significant result from the evaluation of the output parts pertaining to the test light sources 3a, 3b, 3c, both coloured diodes 8, 9 may be activated to indicate to the user that the turbidity of the liquid 6 is very high.

The part of the output from the photo detector 5 pertaining to each of the light sources 3a, 3b, 3c, 4 is compensated or normalised according by mutual comparison in order to compensate for the variation at individual measurements in distance and angle between the light sources 3a, 3b, 3c, 4 and the free surface 12 of the liquid 6. Thus, if the output pertaining to two of the light sources 3a, 3b is relatively low, a correspondingly low output pertaining to the other light sources 3c, 4 is expected.

An analysis based on a multi variable analysis (MVA) of a vast number of test results of mixtures of different alcoholic liquids such as rum, gin and vodka with water, cola, tonic and juice as well as with ice and adding different psychoactive drugs to the liquid mixtures. By the inventor's experiments, it was found that by MVA the presence of a psychoactive drug could be detected with a very high certainty and the drug itself could be identified in more than 8 out of 10 tests.

Further test light sources 3d . . . 3n may be added to increase the certainty with which psychoactive drug may be individually identified and/or to further improve the reliability of the evaluation based on multi variable analysis of previous test results.

In particular, test light sources 3a . . . 3n may in an alternative embodiment or as an addition to the above embodiment be selected to have a wavelength corresponding to a wavelength of significant absorbance by a psychoactive component. As example for ketamine, it was found that the deviation in reflectance of a mixture of water and alcohol with and without the drug was strongest at a wavelength of 778 nm and 6200 nm. The identification of GHB (gamma-hydroxybutyric acid) may be made with test light sources 3a . . . 3n at 1703 nm, 1751 nm or 2292 nm, whereas GBL, which is a chemical conversion of GHB into the corresponding lactone compound gamma-butyrolactone is found to have a significant deviation in reflectance at 1170 nm, 1410 nm, 1683 nm, 1721 nm as well as 1908 nm.

By selecting the wavelength of one or more of the test light sources 3a . . . 3n to match one of these wavelengths significant for a particular psychoactive component or other wavelengths significant for other psychoactive components, the reliability of the evaluation of the tests can be improved, or alternatively, each wavelength of the test light sources 3a . . . 3n is selected as a significant wavelength for one possible psychoactive component, and a further evaluation of the output parts based on a MVA of test results may be added optionally.

REFERENCES

1 Apparatus
2 Bracelet 3a, 3b, 3c Test light sources
3d ... 3n Further test light sources
4 Turbidity light source
5 Photo detector
6 Liquid
7 Control unit
8 Green light diode
9 Red light diode
10 Set of data
11 Transmitter/transceiver
12 Free surface of the liquid
13 Container for liquid
14 Light emitted from a light source
15 Diffusely reflected light
La Wavelength of monochromatic light emitted from first test light source
Lb Wavelength of monochromatic light emitted from second test light source
Lc Wavelength of monochromatic light emitted from third test light source

The invention claimed is:

1. A method of drinking a liquid, the liquid comprising an alcohol in an amount in the range of about 3 to about 50 volume percent, the method comprising:
obtaining the liquid comprising an alcohol in an amount in the range of about 3 to about 50 volume percent;
testing the liquid for the presence of at least the following two psychoactive components: ketamine and gamma-hydroxybutyrate, by:
obtaining a substantially monochromatic light at a first test wavelength selected from the group consisting of 778 nm and 6200 nm by a first test light emitter,
obtaining a substantially monochromatic light at a second test wavelength selected from the group consisting of 1703 nm, 1751 nm, 2292 nm, 1170 nm, 1410 nm, 1683 nm, 1721 nm and 1908 nm by a second test light emitter,
detecting a reflection of the monochromatic light of the first and second test wavelengths on a free surface of the liquid by a photo detector,
wherein the first and the second light emitters are configured such that the first light emitter yields a first output signal from the photo detector in a first output part and the second light emitter yields a second output signal from the photo detector in a second output part, wherein the first and second output signals are separable by a control unit,
analyzing an output signal from the photo detector by the control unit to identify the first output part from the photo detector caused by a reduction in light emitted from the first emitter and the second output part caused by a reduction in light emitted from the second emitter, and
determining from the first and second output parts that the liquid does not comprise any of the at least two psychoactive components; and
drinking the liquid.

2. The method according to claim 1, further comprising the steps of:
emitting a substantially monochromatic light at an at least one additional test wavelength by at least one additional test light emitter,
detecting a reflection of the emitted monochromatic light of the at least one additional test wavelength in a free surface of the liquid by a photo detector,
wherein the first, second and at least one additional light emitters are configured for separation of an output signal from the photo detector in the first, the second, and an at least one additional output parts caused by light emitted from each of the first, second and at least one additional light emitters, respectively,
analyzing an output signal from the photo detector to identify the output parts from the photo detector caused by light emitted from the first, second and at least one additional light emitters, and
applying the first, second and at least one additional output parts to determine an indication of whether the liquid comprises the at least two psychoactive components.

3. The method according to claim 2, wherein the light emitted by the at least one additional light emitter is selected at a turbidity wavelength in the range of about 1400 nm to about 1560 nm, wherein the at least one additional output part from the photo detector caused by light emitted from the at least one additional light emitter is applied for determining the turbidity of the liquid.

4. The method according to claim 3, wherein the turbidity wavelength is in the range of about 1870 nm to about 2050 nm.

5. The method according to claim 2, wherein the at least one additional test wavelength is in the range of about 700 nm to about 2500 nm.

6. The method according to claim 2, wherein the at least one additional test wavelength is in the range of about 900 nm to about 1800 nm.

7. The method according to claim 2, wherein the at least one additional test wavelength is in the range of about 1000 nm to about 1400 nm.

8. The method according to claim 1, further comprising the step of determining from the first, second and at least one additional output parts an indication of the presence of an additional psychoactive component in the liquid, wherein said additional psychoactive component is gamma-butyrolactone.

9. The method according to claim 1, further comprising the step of determining from the first, second and at least one additional output parts an indication of the presence of an additional psychoactive component in the liquid, wherein said additional psychoactive component is at least one of zolpidem, flunitrazepam, zopiclone and methylphenidate.

10. The method according to claim 1, further comprising the step of determining from the first, second and at least one additional output parts an indication of the presence of an additional psychoactive component in the liquid, wherein said additional psychoactive component is at least one of midazolam, temazepam, clonazepam and alprazolam.

11. The method according to claim 1, further comprising the step of determining from the first, second and at least one additional output parts an indication of the presence of an additional psychoactive component in the liquid, wherein said additional psychoactive component is a benzodiazepine.

12. The method according to claim 1, wherein the step of determining from the output parts an indication of whether the liquid comprises the at least two psychoactive components is based on a multi variable analysis of a test results.

13. The method according to claim 1, wherein the liquid is suitable for human consumption after the detecting step.

14. The method according to claim 1, wherein the light emitters and the photo detector are arranged to allow diffuse reflection of light from the free surface of the liquid to reach the photo detector and to avoid specular reflection from the free surface of the liquid to reach the photo detector.

15. The method according to claim 1, wherein at least one of the light emitters is a Light Emitting Diode (LED).

16. The method according to claim 1, wherein the photo detector is comprised of a plurality of photo detecting units.

17. An apparatus comprising:
- a first test light emitter configured to emit a substantially monochromatic light at a first test wavelength selected from the group consisting of 778 nm and 6200 nm,
- a second test light emitter configured to emit a substantially monochromatic light at a second test wavelength selected from the group consisting of 1703 nm, 1751 nm, 2292 nm, 1170 nm, 1410 nm, 1683 nm, 1721 nm and 1908 nm, and
- a photo detector configured to detect a reflection of the emitted monochromatic light of the first and second test wavelengths in a spot on a free surface of a liquid comprising an alcohol in an amount in the range of about 3 to about 50 volume percent;

wherein the first and the second light emitters are configured such that the first light emitter yields a first output signal from the photo detector in a first output part and the second light emitter yields a second output signal from the photo detector in a second output part, wherein the first and second output signals are separable by a control unit, wherein the apparatus is configured for determining from the first and second output parts an indication of whether the liquid comprises at least one psychoactive component by analyzing an output signal from the photo detector by the control unit to identify the first output part from the photo detector caused by a reduction in light emitted from the first emitter and identify the second output part from the photo detector caused by a reduction in light emitted from the second emitter, and wherein the at least one psychoactive component is selected from the group consisting of zolpidem, ketamine and gamma-hydroxybutyrate.

18. The apparatus according to claim 17, wherein the apparatus is provided in a handheld unit.

19. The apparatus according to claim 18, wherein the apparatus is a bracelet.

20. The apparatus according to claim 17, wherein the apparatus comprises about 2 to about 12 test light emitters.

21. The apparatus according to claim 17, wherein the apparatus comprises about 3 to about 8 test light emitters.

22. The apparatus according to claim 17, wherein the apparatus comprises about 3 to about 6 test light emitters.

* * * * *